US012465711B2

(12) United States Patent
Haibach et al.

(10) Patent No.: US 12,465,711 B2
(45) Date of Patent: Nov. 11, 2025

(54) MASK WITH QUICK RELEASE FRAME AND HEADGEAR

(71) Applicant: KONINKLIJKE PHILIPS N.V., Eindhoven (NL)

(72) Inventors: Richard Thomas Haibach, Verona, PA (US); Derrick Blake Andrews, Markleton, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 933 days.

(21) Appl. No.: 17/512,749

(22) Filed: Oct. 28, 2021

(65) Prior Publication Data

US 2022/0193358 A1 Jun. 23, 2022

Related U.S. Application Data

(60) Provisional application No. 63/128,357, filed on Dec. 21, 2020.

(51) Int. Cl.
*A61M 16/06* (2006.01)
*A61M 16/08* (2006.01)

(52) U.S. Cl.
CPC .... *A61M 16/0622* (2014.02); *A61M 16/0683* (2013.01); *A61M 16/0875* (2013.01)

(58) Field of Classification Search
CPC .......... A16M 16/0683; A16M 16/0694; A62B 18/084; A41D 13/1161; A42B 3/08;
(Continued)

(56) References Cited

U.S. PATENT DOCUMENTS 2,414,405 A * 1/1947 Bierman .............. A62B 18/084 128/201.19
2,444,417 A * 7/1948 Bierman ................ A62B 18/00 128/201.19
(Continued)

FOREIGN PATENT DOCUMENTS

CN 106505351 A * 3/2017 ......... H01R 13/4536
DE 102006057763 A1 * 2/2008 ........ A61M 16/0633
(Continued)

OTHER PUBLICATIONS

PE2E Translation Li CN_106505351_A_H (Year: 2017).*
(Continued)

*Primary Examiner* — Brandy S Lee
*Assistant Examiner* — Sydney Reyes Russell
(74) *Attorney, Agent, or Firm* — Michael W. Haas

(57) ABSTRACT

A mask for communicating a flow of breathing gas to an airway of a patient. The mask includes a patient interface having a faceplate and a cushion. The cushion has a first end coupled to the faceplate and an opposite second end for sealingly engaging a portion of the patient's face about one or more airways of the patient. A frame includes a first arm member having a first end coupled to the patient interface via a first coupling arrangement and an opposite second end coupleable to a headgear, and a second arm member having a first end selectively coupled to the patient interface via a second coupling arrangement and an opposite second end coupleable to the headgear. The second coupling arrangement requires a lessor uncoupling force to uncouple than the first coupling arrangement.

12 Claims, 8 Drawing Sheets

(58) Field of Classification Search
CPC ...... A44D 2201/10–40; A44D 2203/00; A44B 11/00; A44B 11/258; A44B 17/00; A44B 17/0041; A61M 16/0683; A61M 16/0694; H01R 13/6205
See application file for complete search history.

(56) References Cited

U.S. PATENT DOCUMENTS

| | | | | |
|---|---|---|---|---|
| 4,848,334 | A | 7/1989 | Bellim | |
| 5,441,046 | A * | 8/1995 | Starr | A61M 16/0683 128/207.11 |
| 8,042,542 | B2 * | 10/2011 | Ging | A61M 16/0616 128/206.28 |
| 2007/0125386 | A1 * | 6/2007 | Quinn | A61M 16/0683 403/399 |
| 2008/0178875 | A1 * | 7/2008 | Henry | A61M 16/0683 128/201.22 |
| 2008/0190432 | A1 | 8/2008 | Blochlinger | |
| 2014/0069433 | A1 * | 3/2014 | Walker | A61M 16/0057 128/206.21 |
| 2015/0000671 | A1 * | 1/2015 | Frerichs | A61M 16/0683 29/428 |
| 2015/0165149 | A1 | 6/2015 | Haibach | |
| 2015/0352308 | A1 | 12/2015 | Cullen | |
| 2016/0067441 | A1 * | 3/2016 | Bearne | A61M 16/0605 128/205.25 |
| 2016/0183620 | A1 * | 6/2016 | Moreau | A42B 3/08 2/421 |
| 2017/0333660 | A1 * | 11/2017 | Haibach | A61M 16/0683 |
| 2018/0084859 | A1 * | 3/2018 | Bancroft | A42B 3/08 |
| 2019/0175863 | A1 | 6/2019 | Hocking | |
| 2020/0046930 | A1 | 2/2020 | Ging | |
| 2020/0338294 | A1 | 10/2020 | Mclauren | |
| 2021/0170134 | A1 | 6/2021 | Freestone | |

FOREIGN PATENT DOCUMENTS

| | | | | |
|---|---|---|---|---|
| EP | 2818194 | A1 * | 12/2014 | A61M 16/06 |
| GB | 144364 | A * | 6/1920 | A44B 17/0088 |
| WO | 2011121466 | A1 | 10/2011 | |
| WO | WO-2012028995 | A1 * | 3/2012 | A61M 16/0057 |
| WO | WO-2013168041 | A1 * | 11/2013 | A61M 16/0605 |
| WO | 2016203376 | A1 | 12/2016 | |
| WO | WO-2018177794 | A1 * | 10/2018 | A61M 16/06 |

OTHER PUBLICATIONS

PE2E Translation Bechtel DE_102006057763_A1_H (Year: 2008).*
International Search Report for PCT/EP2021/086044 filed Dec. 16, 2021.

* cited by examiner

MASK WITH QUICK RELEASE FRAME AND HEADGEAR

CROSS-REFERENCE TO RELATED APPLICATIONS

This patent application claims the priority benefit under 35 U.S.C. § 119(e) of U.S. Provisional Application No. 63/128,357, filed on Dec. 21, 2020, the contents of which are herein incorporated by reference.

BACKGROUND OF THE INVENTION

1. Field of the Invention

The present invention generally relates to masks for use in communicating a flow of breathing gas to an airway of a patient. The present invention further relates to patient interface devices for use in such masks.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation (NIV). It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), chronic obstructive pulmonary disease (COPD), or congestive heart failure (CHF).

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

Typically, patient interface devices include a mask shell or frame having a cushion attached to the shell that contacts the surface of the patient. The mask shell and cushion are held in place by a headgear that wraps around the head of the patient. The mask and headgear form the patient interface assembly. A typical headgear includes flexible, adjustable straps that extend from the mask to attach the mask to the patient.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the interface device be simple to put on and taken off by a patient so that a patient would be more likely to utilize the device as prescribed.

SUMMARY OF THE INVENTION

As one aspect of the invention a mask structured to be coupled to a head of a patient with a headgear for use in communicating a flow of breathing gas to an airway of a patient is provided. The mask comprises a patient interface including: a faceplate, and a cushion having a first end coupled to the faceplate and an opposite second end that is structured to sealingly engage a portion of a face of the patient about one or more airways of the patient. The mask also comprises a frame including: a first arm member having a first end coupled to the patient interface via a first coupling arrangement and an opposite second end structured to be coupled to the headgear, and a second arm member having a first end selectively coupled to the patient interface via a second coupling arrangement and an opposite second end structured to be coupled to the headgear, wherein the second coupling arrangement requires a lessor uncoupling force to uncouple than the first coupling arrangement.

The first frame member may be coupled to the faceplate of the patient interface, and the first end of the second frame member may be coupled to the faceplate of the patient interface.

The first coupling arrangement may provide for the first end of the first arm member to be selectively coupled to the faceplate.

The first end of the cushion and the faceplate may be coupled via over molding.

The first coupling arrangement may comprise: a post member extending outward from the faceplate along a central axis; and an aperture defined in the first end of the first arm member correspondingly shaped to receive the post member.

The post member may include a first feature that interacts with a corresponding second feature of the aperture to constrain the post member within the aperture.

The first feature may comprise a flared region and the second feature is a may be a recessed portion defined in the aperture.

When viewed along the central axis, the post member may have an elongated cross-section.

The second coupling arrangement may comprise: a ridge extending from the first end of the second arm member; and a groove defined in the faceplate that is structured to receive the ridge therein.

The groove may include a plurality of segments comprising: a first segment, a second segment extending generally parallel to the first segment, and a third segment extending between, and generally perpendicular to, the first segment and the second segment, wherein the ridge includes a plurality of segments comprising: a first segment, a second segment extending generally parallel to the first segment of the ridge, and a third segment extending between, and generally perpendicular to, the first segment of the ridge and the second segment of the ridge, and wherein the first, second and third segments of the ridge are sized and positioned to correspondingly engage the first, second and third segments of the groove.

The ridge may comprise a mechanical hook that engages a portion of the groove.

The mechanical hook may comprise an inward angled surface which engages a cooperative angled surface of the groove when the ridge is disposed in the groove.

The mechanical hook may comprise an inward extending protrusion disposed adjacent, and defined in-part by, an outward extending recess that hooks around a protrusion extending into the groove.

The second coupling arrangement may further comprise a first magnetic element positioned in the faceplate and a second magnetic element correspondingly positioned in the second arm member such that the first magnetic element and the second magnetic element are positioned adjacent to each other and attracted toward each other which the ridge is disposed in the groove.

As another aspect of the present invention, a patient interface comprises: a faceplate, and a cushion having a first end coupled to the faceplate and an opposite second end that is structured to sealingly engage a portion of a face of the patient about one or more airways of the patient, wherein the faceplate is structured to be coupled to a first arm member of a frame via a first coupling arrangement, wherein the faceplate is structured to be coupled to a second arm member of the frame via a second coupling arrangement, and wherein the second coupling arrangement requires a lessor uncoupling force to uncouple than the first coupling arrangement.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are provided for the purpose of illustration and description only and are not intended as a definition of the limits of the invention.

DETAILED DESCRIPTION OF THE EXEMPLARY EMBODIMENTS

Figure 1:
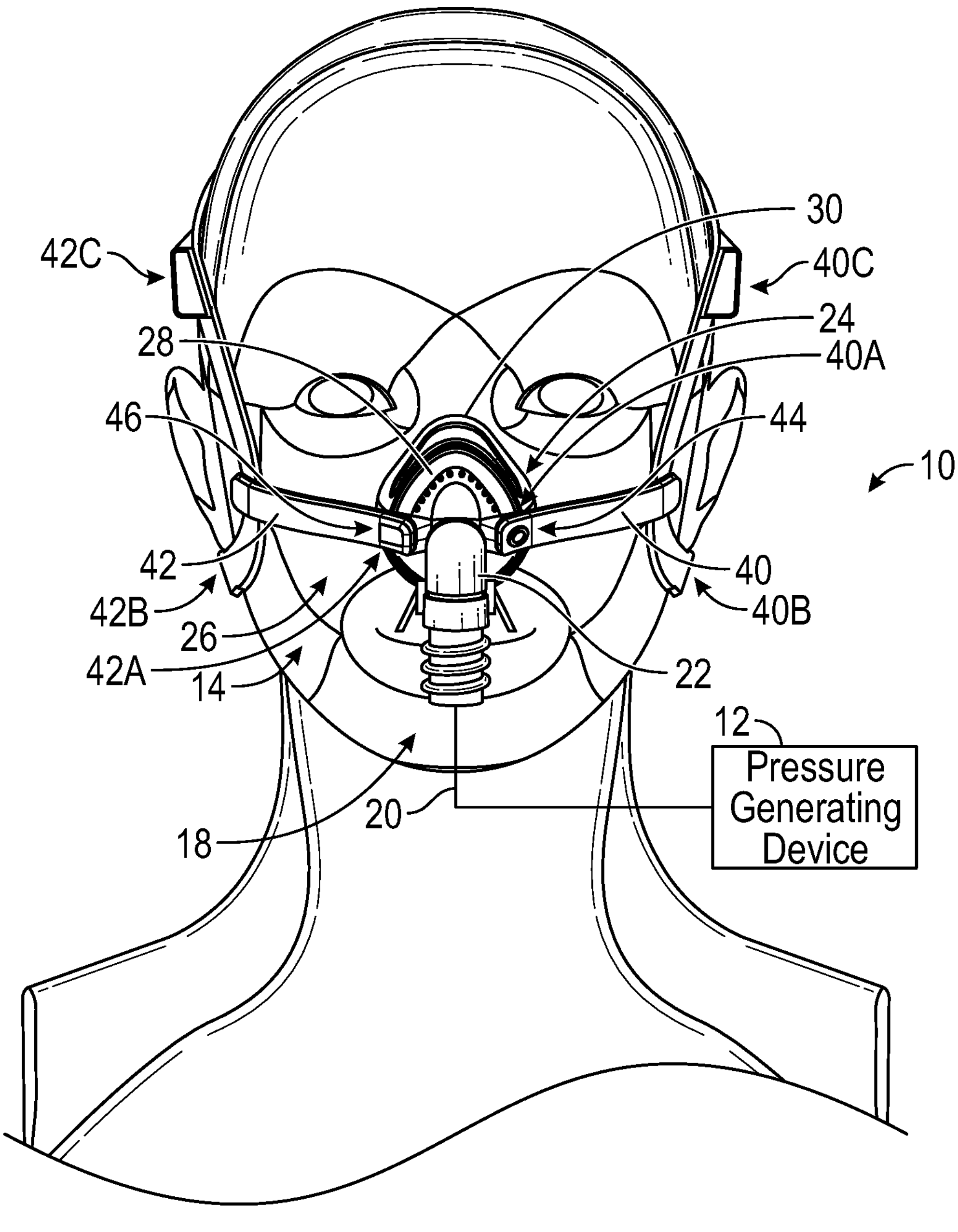
FIG. 1 is a partially schematic view of a system adapted to provide a regimen of respiratory therapy to a patient and includes a front elevation view of an example mask in accordance with the principles of the present invention shown disposed on the head of a patient.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, "selectively coupled" means that two elements are coupled in a manner that can be uncoupled and coupled again without requiring any special tool or tools and without causing damage to either of the elements. As used herein, "permanently coupled" means that two elements are coupled in a manner that cannot be uncoupled without causing damage to one or both of the elements and/or modifying the arrangement in a manner such that the elements cannot be recoupled in the original manner without the use of further materials. For example, elements that are glued, welded, or otherwise bonded would be example of elements that are "permanently coupled".

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality) and the singular form of "a", "an", and "the" include plural referents unless the context clearly indicates otherwise.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
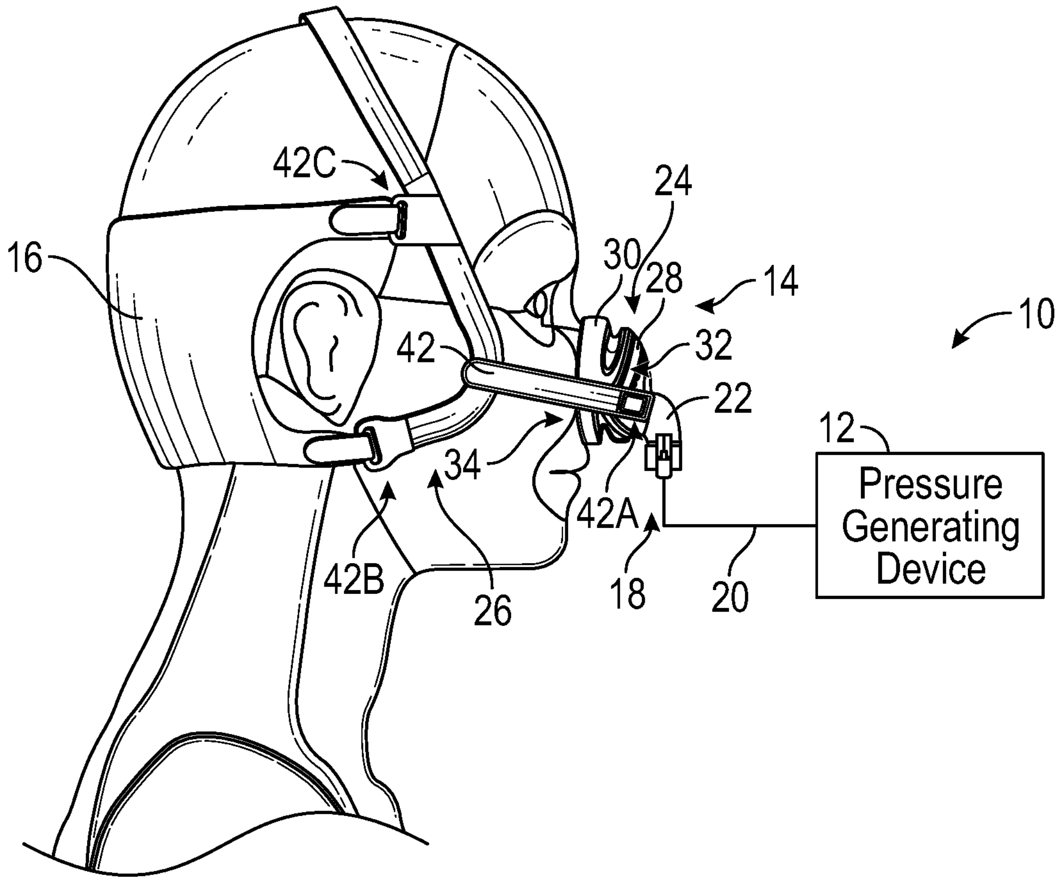
FIG. 2 is a partially schematic view of the system of FIG. 1 including a side elevation view of the mask shown disposed on the head of a patient.
Figure 3:
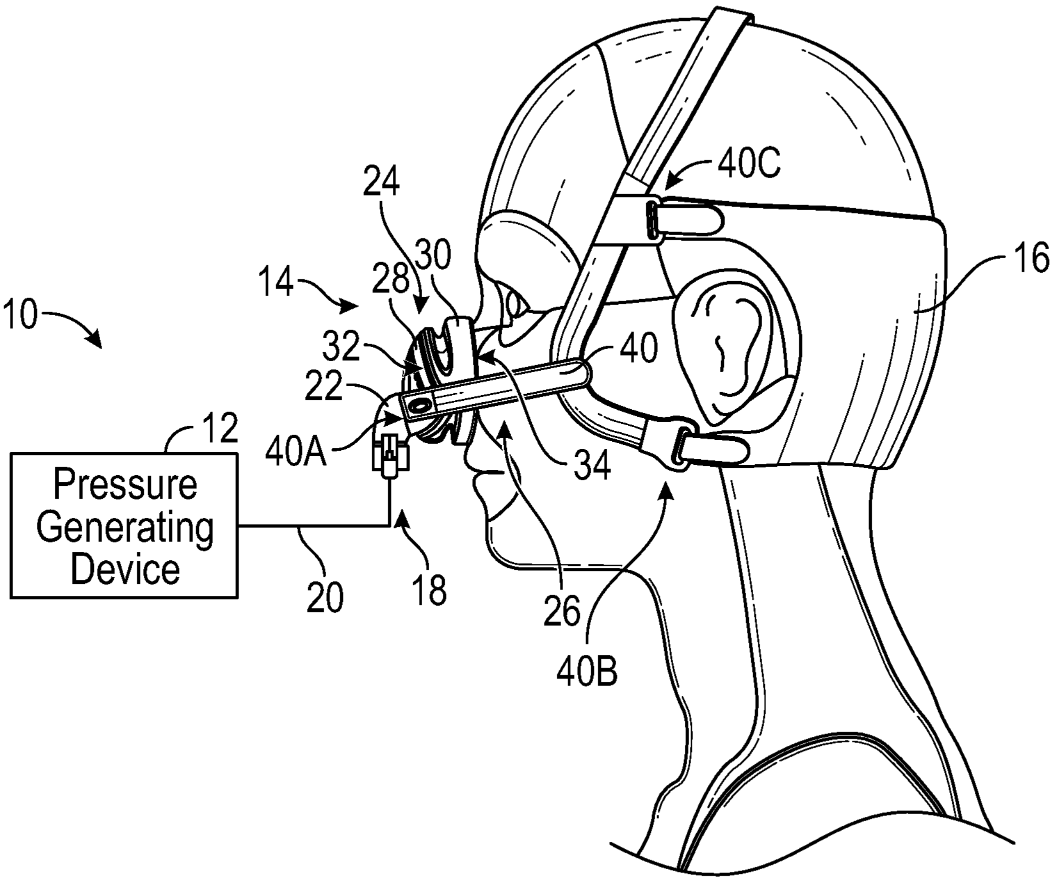
FIG. 3 is a partially schematic view of the system of FIG. 1 including another side elevation view of the mask shown disposed on the head of a patient.

A system 10 adapted to provide a regimen of respiratory therapy to a patient is generally shown in FIGS. 1-3 positioned on the head of a patient (not numbered). System 10 includes a pressure generating device 12 (shown schematically); a mask 14 shown disposed on, and secured to, the head of a patient (not numbered) with a headgear 16; and a patient circuit 18 (partially shown schematically) coupled between pressure generating device 12 and mask 14. Pressure generating device 12 is structured to generate a flow of breathing gas and may include, without limitation, ventilators, constant pressure support devices (such as a continuous positive airway pressure device, or CPAP device), variable pressure devices (e.g., BIPAP®, BiFlex®, or C-Flex™ devices manufactured and distributed by Philips Respironics of Murrysville, Pennsylvania), and auto-titration pressure support devices. Headgear 16 may be of any suitable arrangement and/or material as the example headgear 16 shown in the FIGS. It is thus to be appreciated that headgear 16 is provided in the FIGS. solely for exemplary purposes only to show one example of how mask 14 may be secured to the head of a patient therewith.

Patient circuit 18 is structured to communicate the flow of breathing gas from pressure generating device 12 to mask 14 which then communicates the flow of breathing gas to an airway of the patient. Typically, patient circuit 18 includes a conduit or tube which couples pressure generating device 12 and mask 14. In the example embodiment illustrated in FIGS. 1-3, patient circuit 18 includes a flexible conduit 20 (shown partially schematically) and an elbow 22 coupled to mask 14.

Figure 4:
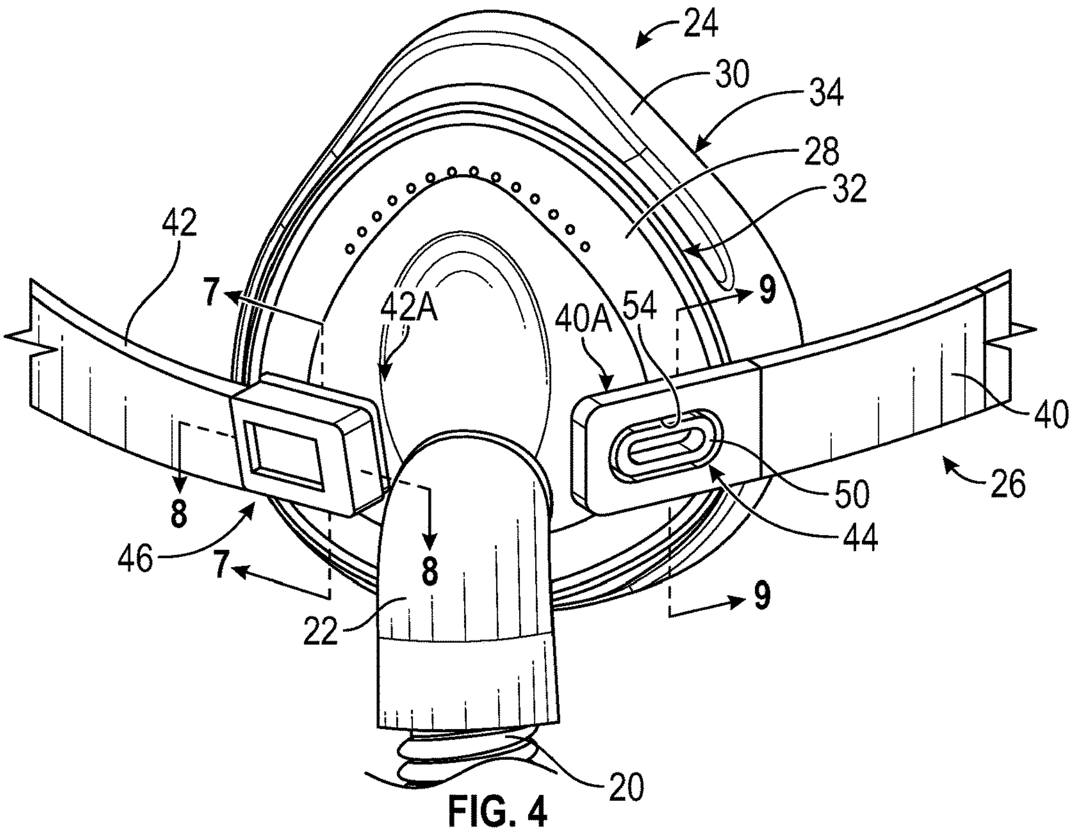
FIG. 4 is a detail front perspective view of a portion of the mask of the system of FIGS. 1-3.

Continuing to refer to FIGS. 1-3, and additionally FIGS. 4 and 5, mask 14 includes a patient interface 24 and a frame 26 coupled thereto that is structured to secure patient interface 24 to the head of the patient via headgear 16, which is also coupled to frame 26 as discussed further below. Patient interface 24 includes a faceplate 28, to which patient circuit 18 is coupled, and a cushion 30. In the example embodiment illustrated in FIGS. 1-5, faceplate 28 is formed from a rigid or semi-rigid material (e.g., without limitation, silicone, plastic), however it is to be appreciated that other suitable materials may be used without varying from the scope of the present invention. Cushion 30 on the other hand is formed from a soft conformable material (e.g., without limitation, silicone) and includes a first end 32 that is coupled to faceplate 28 generally at or about a peripheral edge (not numbered of faceplate 28.

Cushion 30 further includes a second end 34, disposed opposite first end 32, that is structured to sealingly engage a portion of the face of a user about one or more airways of the user. Cushion 30 may be selectably coupled to faceplate 28 or may be generally permanently coupled (e.g., via over molding). In the example embodiment shown in FIGS. 1-5, cushion 30 engages the face of a user about the nose and thus both nostrils of the user, however, it is to be appreciated that embodiments of the present invention may be employed with other cushion arrangements (e.g., without limitation, nasal pillows, oral/nasal mask) without varying from the scope of the present invention. Together faceplate 28 and cushion 30 define a user cavity (not numbered) that is structured to receive the flow of gas produced by pressure generating device 12 and communicated thereto by patient circuit 18.

As mentioned above, mask 14 includes frame 26 that is coupled to patient interface 24 and to headgear 16 for securing patient interface 24 to the head of the patient. More particularly, frame 26 is formed from a semi-rigid or other suitable material (e.g., without limitations, plastic, fabric covered plastic, silicone reinforced with plastic, etc.) and includes a first arm member 40 coupled to, and extending outward in a first direction from patient interface 24 and a separate second arm member 42 coupled to, and extending outward from patient interface 24 in a second direction generally opposite the first direction. In order to provide for patient interface 24 to be readily disposed/secured on—and subsequently be unsecured/removed from—the head of the patient, at least one of arm members 40 or 42 is/are selectively coupled to patient interface. If both arm members 40 and 42 are selectively coupled to patient interface 24 (which desirably allows for patient interface to be swapped out from frame 26 and headgear 16 for cleaning or replacement), one of arm members 40 or 42 is selectively coupled to patient interface 24 in a manner that requires a lesser force to uncouple (i.e., a lesser uncoupling force) than the other arm member 40 or 42 from patient interface 24.

By having only one arm member 40 or 42 selectively coupled, or one arm member 40 or 42 selectively coupled with a lesser uncoupling force, the one arm member 40 or 42 may be uncoupled from patient interface 24 to provide for mask 14 to be removed from the patient or installed on the patient while the patient interface 24 is still coupled/secured with frame 26 and headgear 16 by the other arm member 40 or 42. If both arm members 40 and 42 were uncoupleable with generally the same force, patient interface 24 would tend to undesirably completely uncouple from frame 26 and headgear 16 and fall from the patient (typically to the floor adjacent the patient's bed).

As discussed immediately below, in the one example embodiment shown in FIGS. 1-5, each of arm members 40 and 42 are selectively coupled to faceplate 28 of patient interface 24, with second arm member 42 being selectively coupled via an arrangement that provides for second arm member 42 to be uncoupled from faceplate 28, and thus patient interface 24, more easily (i.e., with a lesser force) than first arm member 40. It is to be appreciated, that one or more of the coupling locations (i.e., on one or both of faceplate 28 and/or cushion 30) and/or coupled arrangements described in conjunction with such embodiment may be varied without varying from the scope of the present invention. It is also to be appreciated that the one of arm member 40 or 42 that is more easily/readily uncoupled from patient interface 24 may be varied without varying from the scope of the present invention.

Continuing to refer to FIGS. 1-5, and additionally FIGS. 6-9, the coupling between each of arm members 40 and 42 of frame 26 and patient interface 24 will now be described in detail. As shown in FIGS. 1-4, first arm member 40 of frame 26 includes a first end 40A that is structured to be coupled to patient interface 24 via a first coupling arrangement 44 and at least one second end 40B (also 40C in the one example shown) disposed opposite first end 40A that is structured to be coupled (preferably via an adjustable arrangement) to headgear 16. Similarly, second arm member 42 of frame 26 includes a first end 42A that is structured to be coupled to patient interface 24 via a second coupling arrangement 46 and at least one second end 42B (also 42C in the one example shown) disposed opposite first end 42A that is structured to be coupled (preferably via an adjustable arrangement) to headgear 16. Although each of the example arm members 40 and 42 shown in FIGS. 1-3 includes two opposite ends 40B, 40C and 42B and 42C, it is to be appreciated that the number of opposite ends may vary (e.g., 1, 3, etc.) without varying from the scope of the present invention.

Referring now to FIGS. 4-9, first coupling arrangement 44 includes a post member 50 that is coupled to, or formed as a portion of, faceplate 28 and extends outward therefrom along a central axis 52 and is structured to interact with a correspondingly shaped aperture 54 defined in first end 40A of first arm member 40 of frame 16. Post member 50 may be formed from thermoplastic or other suitable material or materials and depending on the materials used may formed as a hollow member (such as shown) or as a solid member. Post member 50 includes a first feature 56 that interacts with a corresponding second feature 58 of aperture 54 to constrain/couple (either selectively or permanently) post member 50 within aperture 54. In the one example shown, first feature 56 is a flared region that interacts with second feature 58 formed as a recessed portion of aperture 54, however, it is to be appreciated that other features 56, 58 may be utilized without varying from the scope of the present invention.

In the example shown in the figures, post member 50 (and correspondingly aperture 54) has an elongated cross-section when viewed along axis 52 such that when post member 50 is positioned in aperture 54 of first arm member 40 rotation of first arm member 40 with respect to faceplate 28 (and thus patient interface 24) is limited/prevented to a degree or less. As an alternate embodiment to the arrangement shown in the figures, the elements of first coupling arrangement 44 may be reversed (i.e., post 50 on first arm member 40 and aperture 54 defined in faceplate 28) without varying from the scope of the present invention.

Figure 5:
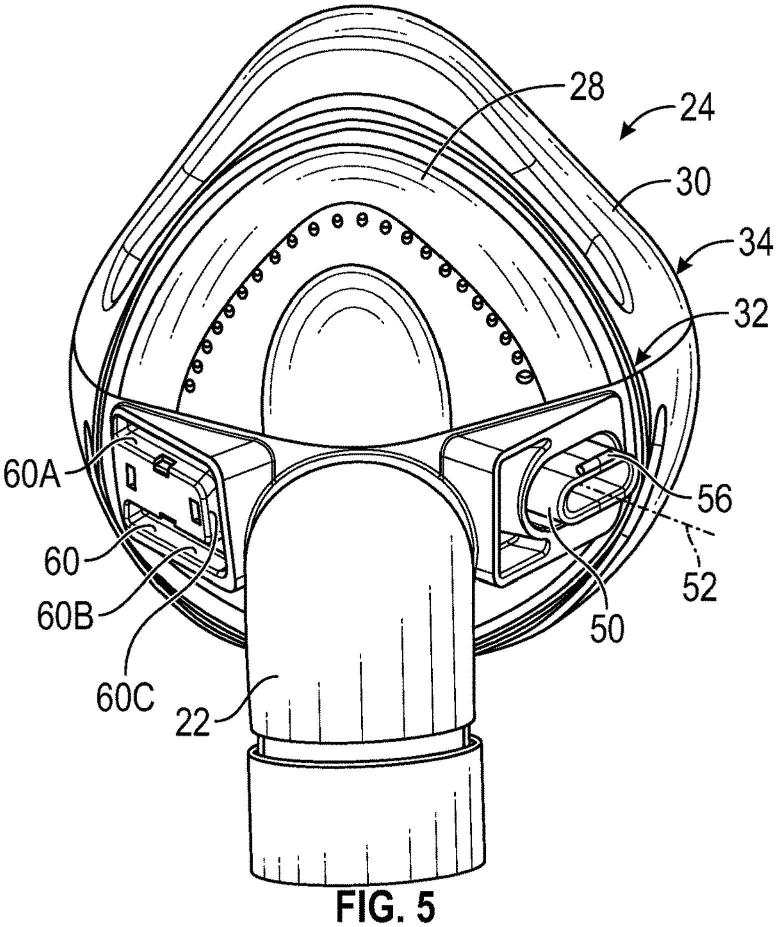
FIG. 5 is a front perspective view of the patient interface of the mask of FIGS. 1-4.
Figure 6:
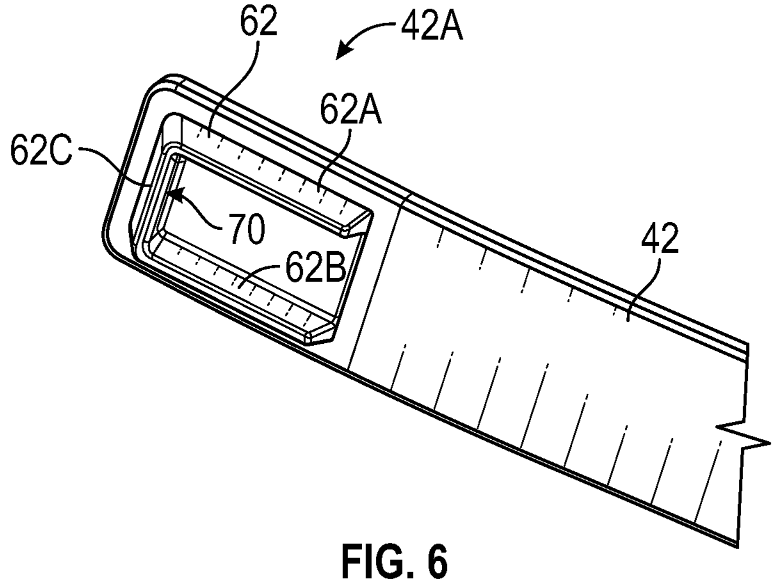
FIG. 6 is a detail portion of an engagement portion of a frame member of the mask of FIGS. 1-4.

Continuing to refer to FIGS. 4-9, second coupling arrangement 46 includes a groove 60 defined in faceplate 28 that is structured to receive a ridge 62 extending from first end 42A of second arm member 42. As shown in FIG. 5, in the illustrated example groove 60 includes a plurality of segments including: a first segment 60A, a second segment 60B extending generally parallel to first segment 60A, and a third segment 60C extending between, and generally perpendicular to, first and second segments 60A and 60B. Similarly, ridge 62 includes a plurality of corresponding segments including: a first segment 62A, a second segment 62B extending generally parallel to first segment 62A, and a third segment 62C extending between, and generally perpendicular to, first and second segments 62A and 62B. Similar to the function of the elongated cross-sections of first coupling arrangement 44 previously discussed, each of first and second segments 60A, 60B and 62A, 62B of first coupling arrangement 44 serve to limit/prevent rotation of second arm member 42 with respect to faceplate 28 (and thus patient interface 24) to a degree or less.

Figure 8:
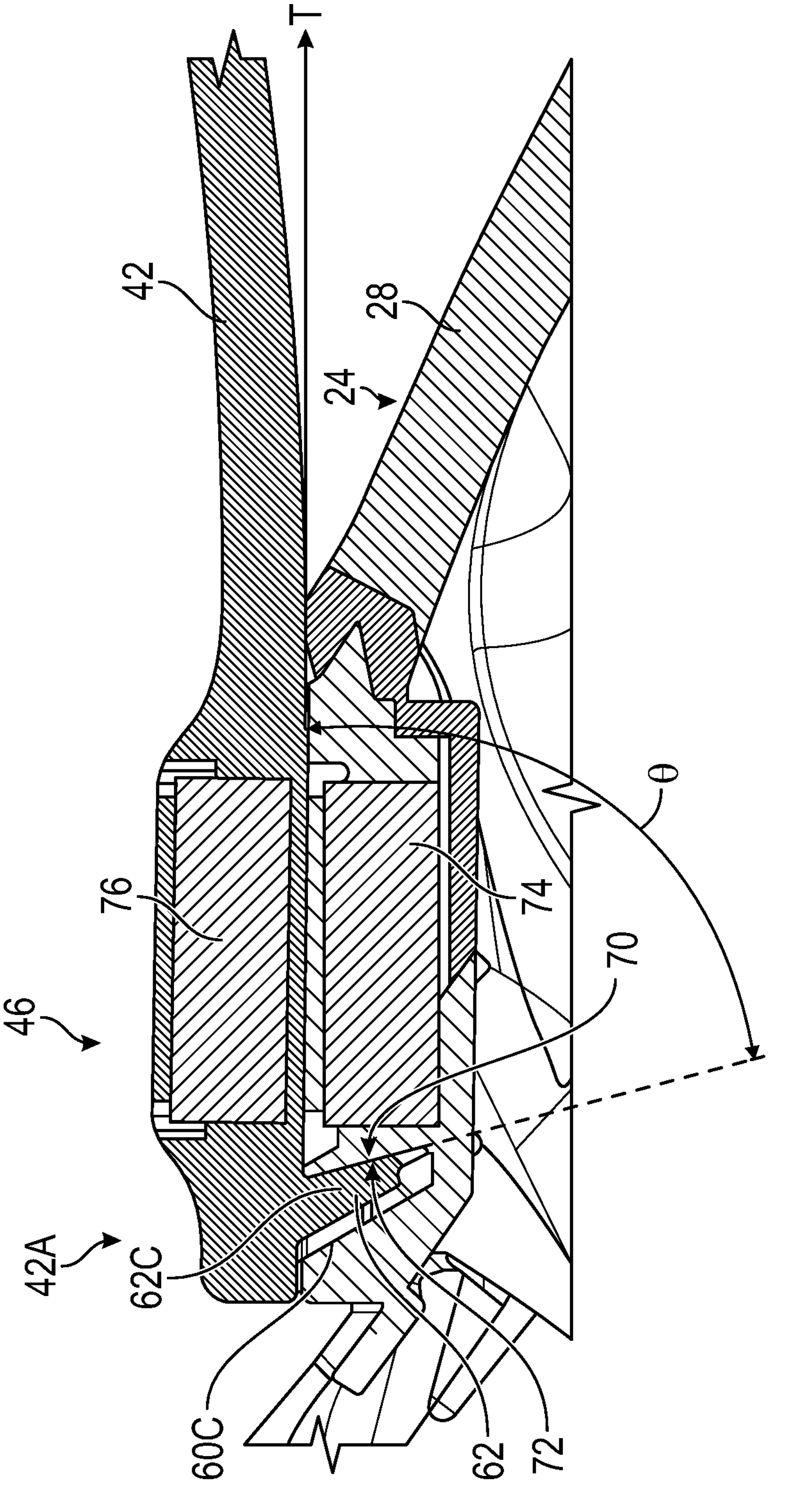
FIG. 8 is a sectional view of the mask of FIGS. 1-4 taken along line 8-8 of FIG. 4.
Figure 9:
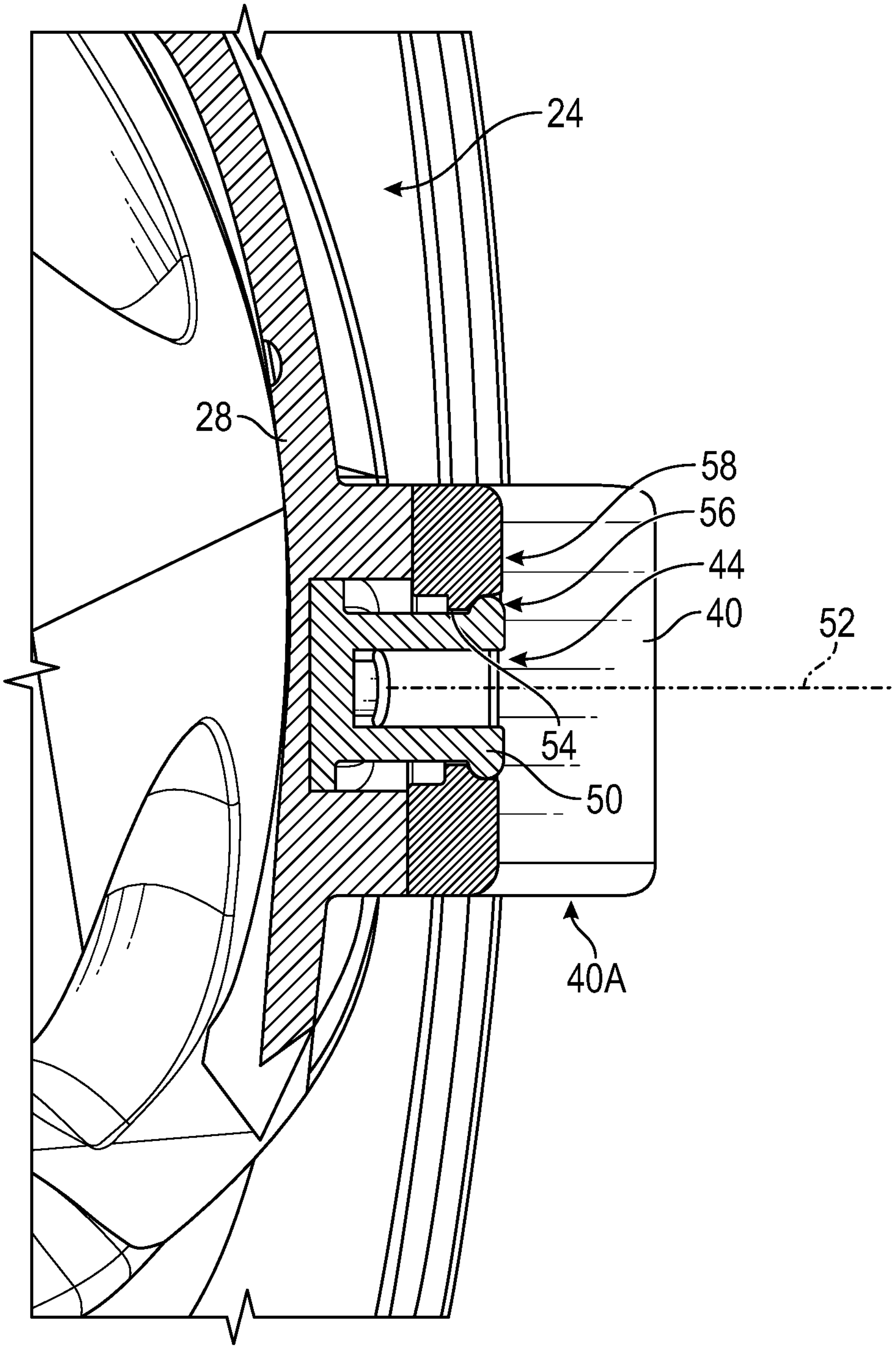
FIG. 9 is a sectional view of the mask of FIGS. 1-4 taken along line 9-9 of FIG. 4.

In place of, or in addition to, having multiple segments 60A-60C and 62A-62C, second coupling arrangement 46 may include a mechanical hook or interlock arrangement (not numbered), which in the example shown in FIG. 8 is an inward angled surface 70 provided on ridge 62 that engages a cooperative angled surface 72 of groove 60. Angled surface 70 is disposed at an angle θ less than 90° from a pull vector T that would be exerted on second arm member by tightening of headgear 16. It is thus to be appreciated that angled surface 70 functions generally as a hook when second arm member 42 is tensioned in the direction T (FIG. 8) by tightening of headgear 16.

Figure 10:
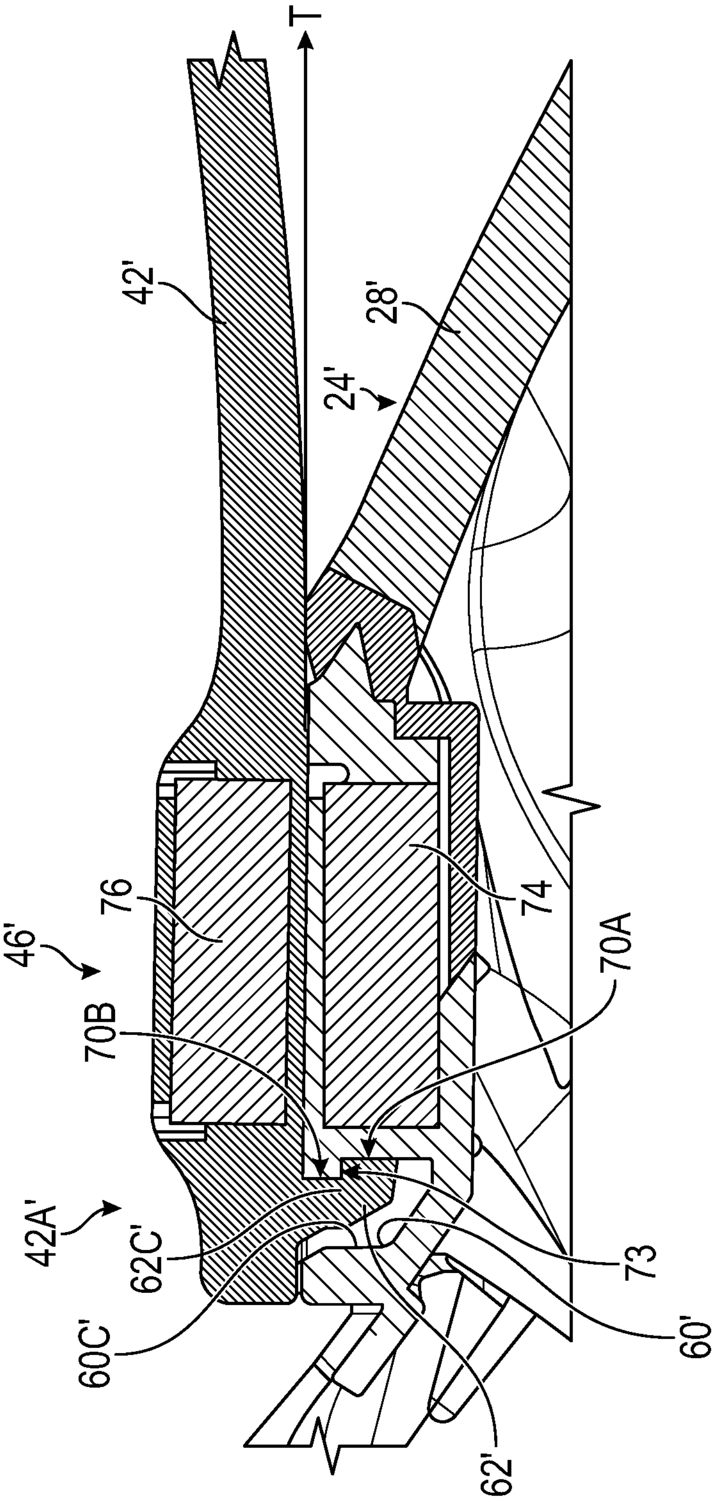
FIG. 10 is a sectional view of an alternative embodiment of the mask of FIGS. 1-4 taken along a line similar to 8-8 of FIG. 4.

An example of an alternative mechanical hook or interlock arrangement is shown in FIG. 10, which is a similar view as that shown in FIG. 8 and in which similar elements are shown labeled with similar numbering as FIG. 8 and not described again. In such example embodiment as shown in FIG. 10, instead of an inward angled surface 70, ridge 62' includes an inward extending (i.e., generally back toward the majority of second arm member 42') protrusion 70A positioned at a peak (not numbered) of ridge 62' disposed adjacent, and defined in-part by, an outward (i.e., generally away from the majority of second arm member 42') extending recess 70B. Together protrusion 70A and recess 70B function generally as a mechanical hook that hooks around a protrusion 73 extending into segment 60C' of groove 60' (i.e., into segment 60C' away from the majority of second arm member 42').

Figure 7:
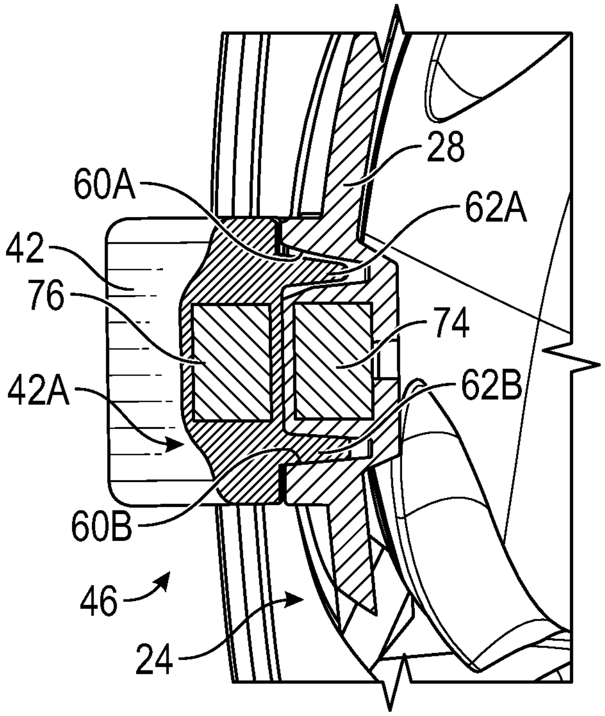
FIG. 7 is a sectional view of the mask of FIGS. 1-4 taken along line 7-7 of FIG. 4.

As shown in FIGS. 7 and 8, second coupling arrangement 46 further includes a first magnetic element 74 positioned in faceplate 28 and a second magnetic element 76 correspondingly positioned in second arm member 42 such that first and second magnetic elements are attracted toward each other. In the example shown in FIGS. 7 and 8, each of magnetic elements 74 and 76 comprise magnets, however, it is to be appreciated that one of magnetic elements 74 and 76 may instead be a material to which a magnet would be attracted without varying from the scope of the present invention. As an alternate embodiment to the arrangement shown in the figures, the elements of second coupling arrangement 46 may be reversed, i.e., groove 60 defined in first arm member 42 and ridge 62 defined in faceplate 28, without varying from the scope of the present invention. It is to be appreciated that in such alternate version, angled surface 70 of ridge 62 would be on the opposite side of ridge 62 and angled toward a center plane of faceplate 28 in order to provide a hook onto which second arm member 42 would hook (and resist tensioning of second arm member in the direction T shown in FIG. 8).

From the foregoing it is thus to be appreciated that embodiments of the present invention provide improved coupling arrangements for use in securing a patient interface device to the head of a patient that may be readily coupled or uncoupled by a patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word “comprising” or “including” does not exclude the presence of elements or steps other than those listed in a claim. In a device claim enumerating several means, several of these means may be embodied by one and the same item of hardware. The word “a” or “an” preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A mask structured to be coupled to a head of a patient with a headgear for use in communicating a flow of breathing gas to an airway of a patient, the mask comprising:

(a) a patient interface including:
  a faceplate, and
  a cushion having a first end coupled to the faceplate and an opposite second end that is structured to sealingly engage a portion of a face of the patient about one or more airways of the patient; and (b) a frame including:
  a first arm member having a first end coupled to the patient interface via a first coupling arrangement and an opposite second end structured to be coupled to the headgear, and
  a second arm member having a first end selectively coupled to the patient interface via a second coupling arrangement and an opposite second end structured to be coupled to the headgear, wherein the second coupling arrangement requires a lesser lesser uncoupling force to uncouple than the first coupling arrangement wherein the second coupling arrangement comprises:
  a ridge extending from the first end of the second arm member; and
  a groove defined in the faceplate that is structured to receive the ridge therein,
  wherein the groove includes a plurality of segments comprising: a first segment, a second segment extending generally parallel to the first segment, and a third segment extending between, and generally perpendicular to, the first segment and the second segment,
  wherein the ridge includes a plurality of segments comprising: a first segment, a second segment extending generally parallel to the first segment of the ridge, and a third segment extending between, and generally perpendicular to, the first segment of the ridge and the second segment of the ridge, and wherein the first, second, and third segments of the ridge are sized and positioned to correspondingly engage the first, second and third segments of the groove.

2. The mask of claim 1, wherein the first end of the first arm member is coupled to the faceplate of the patient interface, and wherein the first end of the second frame arm member is coupled to the faceplate of the patient interface.

3. The mask of claim 1, wherein the first coupling arrangement provides for the first end of the first arm member to be selectively coupled to the faceplate.

4. The mask of claim 1, wherein the first end of the cushion and the faceplate are coupled via over molding.

5. The mask of claim 1, wherein the first coupling arrangement comprises:

a post member configured to extend outward from the faceplate along a central axis; and an aperture defined in the first end of the first arm member correspondingly shaped to receive the post member.

6. The mask of claim 5, wherein the post member includes a first feature that interacts with a corresponding second feature of the aperture to constrain the post member within the aperture.

7. The mask of claim 6, wherein the first feature comprises a flared region and the second feature is a recessed portion defined in the aperture.

8. The mask of claim 7, wherein viewed along the central axis, the post member has an elongated cross-section.

9. The mask of claim 1, wherein the ridge comprises a mechanical hook that engages a portion of the groove.

10. The mask of claim 9, wherein the mechanical hook comprises an inward angled surface which engages a cooperative angled surface of the groove when the ridge is disposed in the groove.

11. The mask of claim 9, wherein the mechanical hook comprises an inward extending protrusion disposed adjacent, and defined in-part by, an outward extending recess that hooks around a protrusion extending into the groove.

12. The mask of claim 1, wherein the second coupling arrangement further comprises a first magnetic element positioned in the faceplate and a second magnetic element correspondingly positioned in the second arm member such that the first magnetic element and the second magnetic element are configured to be positioned adjacent to each other and attract toward each other when the ridge is disposed in the groove.

* * * * *